(12) United States Patent
Karasiuk

(10) Patent No.: US 8,721,662 B2
(45) Date of Patent: *May 13, 2014

(54) SKIN TREATMENT SYSTEM AND METHOD OF USE

(75) Inventor: Kenneth B. Karasiuk, Oak Park, CA (US)

(73) Assignee: Envy Medical, Inc., Westlake Village, CA (US)

( * ) Notice: Subject to any disclaimer, the term of this patent is extended or adjusted under 35 U.S.C. 154(b) by 1 day.

This patent is subject to a terminal disclaimer.

(21) Appl. No.: 13/149,594

(22) Filed: May 31, 2011

(65) Prior Publication Data

US 2012/0136374 A1 May 31, 2012

Related U.S. Application Data

(63) Continuation of application No. 11/562,892, filed on Nov. 22, 2006, now Pat. No. 7,951,156, which is a continuation-in-part of application No. 10/393,682, filed on Mar. 19, 2003, now Pat. No. 7,658,742, which is a continuation-in-part of application No. 09/989,992, filed on Nov. 21, 2001, now Pat. No. 6,695,853.

(51) Int. Cl.
*A61B 17/50* (2006.01)

(52) U.S. Cl.
USPC .............................................. 606/131

(58) Field of Classification Search
USPC ......... 606/131, 132, 114, 127, 128, 133, 167; 604/289, 290, 313, 315, 319; 601/6, 7; 132/200, 212; 451/36, 75
See application file for complete search history.

(56) References Cited

U.S. PATENT DOCUMENTS

| | | | |
|---|---|---|---|
| 882,532 | A | 3/1908 | McCall |
| 1,882,040 | A | 10/1932 | Roehm |
| 1,898,652 | A | 2/1933 | Williams |
| 2,228,676 | A | 1/1941 | Renga |
| 2,266,931 | A | 12/1941 | Wheeler |
| 2,338,339 | A | 1/1944 | LaMere et al. |
| 2,608,032 | A | 8/1952 | Garver |
| 2,655,146 | A | 10/1953 | Force, Jr. |
| 2,701,559 | A | 2/1955 | Cooper |
| 2,712,823 | A | 7/1955 | Kurtin |
| 2,867,214 | A | 1/1959 | Wilson |
| 2,881,763 | A | 4/1959 | Robbins |

(Continued)

FOREIGN PATENT DOCUMENTS

| | | |
|---|---|---|
| DE | 3421390 | 12/1985 |
| EP | 0258901 | 9/1988 |

(Continued)

*Primary Examiner* — Pedro Philogene
*Assistant Examiner* — David Comstock
(74) *Attorney, Agent, or Firm* — Aka Chan LLP

(57) ABSTRACT

A device, a system employing the device, and method of performing skin treatment are provided for skin treatment. The device includes a vacuum head base defining a chamber therein and having a substantially smooth treatment tip attached and extending from an end thereof or integral therewith. The tip has at least one central opening that is open to the chamber, and is adapted to contact the skin and traverse the skin in a substantially nonabrasive manner. A vacuum access opening is provided through a side wall of the vacuum head base and adapted to connect with a source of vacuum. A tissue stop member is located within the chamber. It may have an abrasive surface for exfoliating skin cells, or a smooth surface for traversing the skin without substantial abrasion.

20 Claims, 7 Drawing Sheets

(56) References Cited

U.S. PATENT DOCUMENTS

| | | |
|---|---|---|
| 2,921,585 A | 1/1960 | Schumann |
| 3,085,573 A | 4/1963 | Meyer et al. |
| 3,236,231 A | 2/1966 | Schneider et al. |
| 3,476,112 A | 11/1969 | Elstein |
| 3,574,239 A | 4/1971 | Sollerud |
| 3,715,838 A | 2/1973 | Young et al. |
| 3,736,921 A | 6/1973 | Kawada |
| 3,818,904 A | 6/1974 | Kawada |
| 3,841,322 A | 10/1974 | Spelio |
| 3,841,323 A | 10/1974 | Stoughton |
| 3,964,212 A | 6/1976 | Karden |
| 4,003,373 A | 1/1977 | Spelio |
| 4,182,329 A | 1/1980 | Smit et al. |
| 4,216,233 A | 8/1980 | Stein |
| 4,241,499 A | 12/1980 | Perrone |
| 4,378,804 A | 4/1983 | Cortese, Jr. |
| 4,560,373 A | 12/1985 | Sugino et al. |
| 4,572,187 A | 2/1986 | Schetrumpf |
| 4,646,480 A | 3/1987 | Williams |
| 4,676,749 A | 6/1987 | Mabille |
| 4,706,676 A | 11/1987 | Peck |
| 4,754,756 A | 7/1988 | Shelanski |
| 4,757,814 A | 7/1988 | Wang et al. |
| 4,836,192 A | 6/1989 | Abbate |
| 4,900,316 A | 2/1990 | Yamamoto |
| 4,917,086 A | 4/1990 | Feltovich et al. |
| 4,957,747 A | 9/1990 | Stiefel |
| 5,012,797 A | 5/1991 | Liang et al. |
| 5,037,431 A | 8/1991 | Summers et al. |
| 5,037,432 A | 8/1991 | Molinari |
| 5,100,412 A | 3/1992 | Rosso |
| 5,207,234 A | 5/1993 | Rosso |
| 5,377,701 A | 1/1995 | Fang |
| 5,562,643 A | 10/1996 | Johnson |
| 5,699,810 A | 12/1997 | Pallikaris |
| 5,800,446 A | 9/1998 | Banuchi |
| 5,810,842 A | 9/1998 | DiFiore et al. |
| 5,873,881 A | 2/1999 | McEwen et al. |
| 5,971,999 A | 10/1999 | Naldoni |
| 6,039,745 A | 3/2000 | DiFiore et al. |
| 6,042,552 A | 3/2000 | Cornier |
| 6,080,165 A | 6/2000 | DeJacma |
| 6,080,166 A | 6/2000 | McEwen et al. |
| 6,136,008 A | 10/2000 | Becker et al. |
| 6,139,553 A | 10/2000 | Dotan |
| 6,162,232 A | 12/2000 | Shadduck |
| 6,196,982 B1 | 3/2001 | Ball |
| 6,214,009 B1 | 4/2001 | Toriumi et al. |
| 6,241,739 B1 | 6/2001 | Waldron |
| 6,299,620 B1 | 10/2001 | Shadduck et al. |
| 6,319,211 B1 | 11/2001 | Ito et al. |
| 6,387,103 B2 | 5/2002 | Shadduck |
| 6,423,078 B1 | 7/2002 | Bays et al. |
| 6,500,183 B1 | 12/2002 | Waldron |
| 6,511,486 B2 | 1/2003 | Mercier et al. |
| 6,629,983 B1 | 10/2003 | Ignon |
| 6,641,591 B1 | 11/2003 | Shadduck |
| 6,942,649 B2 | 9/2005 | Ignon et al. |
| 2002/0016601 A1 | 2/2002 | Shadduck |
| 2002/0107527 A1 | 8/2002 | Burres |
| 2004/0143274 A1 | 7/2004 | Shadduck |

FOREIGN PATENT DOCUMENTS

| | | |
|---|---|---|
| IT | 1184922 | 10/1987 |
| WO | 99/23951 A1 | 5/1999 |
| WO | 0067692 | 11/2000 |

FIG. 8A
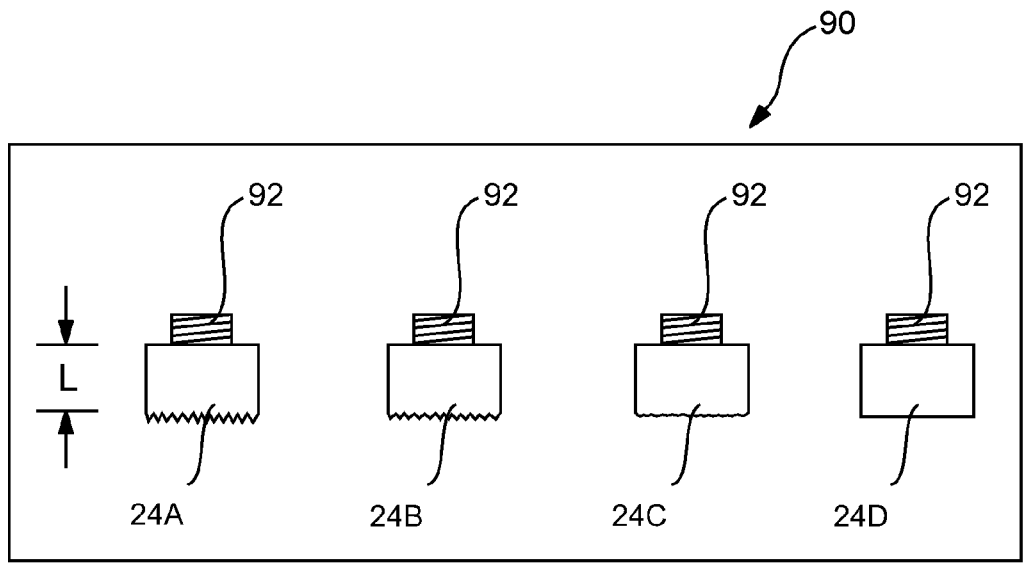
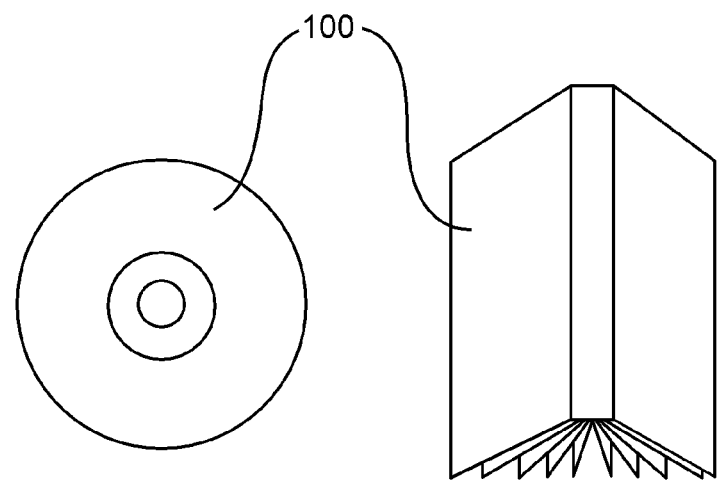
FIG. 8B

SKIN TREATMENT SYSTEM AND METHOD OF USE

CROSS-REFERENCE TO RELATED APPLICATIONS

This application is a continuation of U.S. patent application Ser. No. 11/562,892, filed on Nov. 22, 2006, issued as U.S. Pat. No. 7,951,156 on May 31, 2011, which is a continuation of U.S. patent application Ser. No. 10/393,682, filed on Mar. 19, 2003, issued as U.S. Pat. No. 7,658,742 on Feb. 9, 2010, which is a continuation-in-part of U.S. patent application Ser. No. 09/989,992, filed on Nov. 21, 2001, issued as U.S. Pat. No. 6,695,853 on Feb. 24, 2004, which are incorporated by reference.

BACKGROUND OF THE INVENTION

The present invention relates to the field of dermatology, more particularly to skin treatment and conditioning.

Microdermabrasion is a process for removing dead cells from the outermost layer of the skin (the epidermis) to provide a younger and healthier looking appearance, remove wrinkles, clean out blocked pores, remove some types of undesirable skin conditions that can develop, and enhance skin tone. The process of microdermabrasion should be performed with a certain degree of accuracy, so that underlying live layers of skin tissue are not removed or damaged, but that enough dead cells are removed to give effective results.

Abrasive tipped devices or rotating brushes and cylinders coated with abrasive particles, such as diamond dust, have been used to remove skin layers. U.S. Pat. No. 2,712,823 discusses a brush for removing skin blemishes which includes rotating metallic bristles. This device is more properly referred to as a dermabrasion device as it is quite aggressive in the amounts and rates of tissues removed. While this type of device can be effective for removing gross scarring and keloids such as those associated with burn victims, it can also cause scarring and is difficult to accurately control with regard to amounts of tissue removed. As such it is incapable of effectively performing microabrasion as it is currently defined in the art. U.S. Pat. No. 2,867,214 similarly discusses a device that employs motor driven stainless steel wire brushes and cannot effectively perform microdermabrasion.

U.S. Pat. No. 4,241,499 discusses a handheld foot care instrument that includes a roughened dermabrasion undersurface to function as a nail file and skin smoother While this device may be effective for "spot treatment" of calluses, corns, and the like on the foot, it would not be an effective tool for an overall microdermabrasion treatment of the face or other large area of skin that must be treated with a consistent amount of abrasion over an entire surface.

U.S. Pat. No. 4,378,804 is directed to a skin abrasion device which uses flowing water to rotate an abrasive brush and create a vacuum to remove loosened skin particles. The rotating brush is usually used in conjunction with a liquid detergent or medicinal compound applied to the skin surface being scrubbed.

U.S. Pat. No. 4,572,187 discusses a dermabrasion tool that employs a rotary hub and a plurality of flexible strips each having a single abrasive surface. No means are disclosed for conditioning the skin or of removing the dead skin particles from the surface of the skin after they have been abraded.

U.S. Pat. No. 4,957,747 discusses the use of powdered aluminum oxide or a liquid topical composition containing suspended aluminum oxide which is applied to the skin to abrade it. U.S. Pat. No. 5,971,999 discusses a microdermabrasion system which employs a jet of a mixture of air and reducing crystals, such as aluminum oxide, that is applied to the skin to perform the microdermabrasion. U.S. Pat. No. 5,012,797 discusses the use of chemicals or ultrasonically oscillating tips to perform abrasion.

U.S. Pat. No. 5,037,431 describes the use of a pressurized jet of a liquid, such as water or sterile saline, to fragment and remove diseased tissue without harming surrounding healthy tissue. This device operates in conjunction with vacuum aspiration to remove the liquid and fragmented tissue. A powdered abrasive material may be applied to abrade the skin and removal may be performed using vacuum.

U.S. Pat. No. 6,241,739 discusses a microdermabrasion device that provides a tubular treatment tool having a fixed abrasive tip on the end thereof. The abrasive tip has a central opening therethrough, through which a vacuum is applied. When the tip is scraped over the surface of the skin, loosened skin particles are vacuumed up through the central opening. However, a trailing side of the abrasive tip, which trails the central opening of the abrasive tip as the tip is moved over the surface of the skin, also microabrades the skin surface and leaves a trail of loosened skin particles which cannot be collected by the vacuum. Additionally, this is a dry system which does not treat the skin during microdermabrasion, which can leave streaking effects on the remaining skin.

While microdermabrasion is often useful, it is sometimes desired to effect skin treatment utilizing vacuum without abrasion. Various vacuum-based therapies and devices have been developed to treat the skin and subdermal tissues by way of massage or vacuum action, or a combination of these. One such therapy, as discussed in U.S. Pat. No. 3,841,332, involves cup shaped members drawn over the skin in which a pulsating vacuum results in a cyclical suction and relaxation action. The therapy is said to promote lymphatic and blood circulation in the areas of suction application. A similar approach is described in U.S. Pat. No. 6,319,211, especially for removing dirt and debris.

In order to facilitate vacuum-based tissue massage or pursue other treatment goals, or both, a technician utilizing a suction device will often topically apply a lubricant such a gel, massage oil, or another solution. It is also know to utilize suction devices adapted to deliver such materials through or within the vacuum chamber defined by the working end of the instrument.

Yet, none of the aforementioned references teach a system that incorporates the various advantages of the present invention. For example, no instrument or system adapted to perform microderabrasion includes provision for delivery of a therapeutically useful solution at the abraded site. Instead, useful agents are applied as a lotion, salve or balm, after moving the treatment device or terminating its use altogether. The present invention offers an improved approach for skin treatment. Particularly, it is a system offering additional or optional advantages in the context of vacuum massage, dermal abrasion, or point delivery, or a combination of these, of a desired compound.

BRIEF SUMMARY OF THE INVENTION

The present invention is directed to a microdermabrasion device, microdermabrasion system employing the device, and method of performing microdermabrasion. It is further directed to vacuum massage devices. It is especially applicable in either context for therapeutic fluid delivery.

A device for exfoliating skin cells from an external surface of skin includes a vacuum head base defining a chamber therein and having a substantially smooth treatment tip attached and extending from an end thereof or integral therewith. The tip has at least one central opening which is open to the chamber, and is adapted to contact the skin and traverse the skin in a substantially nonabrasive manner. A vacuum access opening is provided through a side wall of the vacuum head base and adapted to connect with a source of vacuum. An abrasive member may be located within the chamber, and at least one opening adapted to allow the flow of one or more fluids through the chamber is provided, where upon application of vacuum through the vacuum access opening, the fluids are drawn though the chamber, applied to the skin and taken up through the vacuum access opening, and a portion of the skin, targeted by the tip opening, is drawn into the chamber and brought into contact with the abrasive member.

A system for performing microabrasion is provided which includes an applicator tool having a substantially nonabrasive tip with at least one opening therethrough, the tip being adapted to contact the skin of a patient; an abrasive member located internally of the applicator tool, and means for applying vacuum through the at least one opening, where upon application of vacuum a portion of the skin is drawn into contact with the abrasive member.

Means for delivering fluid through the applicator tool and the at least one tip opening are provided, for application of the fluid to the skin.

A system for performing microabrasion according to the present invention includes an applicator tool having a longitudinal axis and a substantially nonabrasive tip with at least one opening therethrough. A conduit extends into the applicator tool and an abrasive member is mounted on an end of the conduit and located internally of the applicator tool. A vacuum access opening is provided through a side wall of the tool, for connection with a source of vacuum to apply vacuum to a tip opening.

The abrasive member or a nonabrasive member seals off the end of the conduit which is located internally of the applicator tool, and at least one opening is provided through a wall of the conduit. In either case, the member that seals off the conduit is positioned relative to the tip opening to serve as a limiting surface with respect to tissue drawn into the device by vacuum. The abrasive member is textured to enable microdermabrasion. The nonabrasive member preferably has a surface finish that avoids such action. Still, the system may be provided with a conduit sealing member of any of a range or spectrum of abrasiveness ranging from (substantially) zero, to a maximum level suited for microdermabrasion. To maximize device utility, the sealing member is preferably removable or interchangeable with others to offer a variety of functions or treatment options, or combination of these.

A fluid reservoir adapted to hold treatment liquids may be connected to the conduit, where, upon application of vacuum through the vacuum access opening, the treatment liquids are drawn through the conduit and delivered to the at least one opening in the tip.

A collection reservoir is connected to the vacuum access opening via a vacuum line for collection of the fluids and microabraded skin cells and is in turn connected to a vacuum source. A filter may be connected inline between the collection reservoir and the vacuum source.

A method of performing microabrasion is provided which includes: applying a nonabrasive treatment tip to a skin surface; providing negative pressure through an opening in the treatment tip to establish a relative vacuum; drawing a portion of the skin surface through the opening and into contact with an abrasive member; and moving the nonabrasive treatment tip over the skin surface and microabrading the portion of the skin in contact with the abrasive member.

Microabraded skin particles are collected through a vacuum conduit through which the negative pressure is provided. Fluid may be applied to the skin though the opening in the treatment tip. In such instances, the vacuum conduit will also collect excess fluid.

The vacuum provided by the negative pressure surrounds a perimeter of the abrasive, moderately abrasive or nonabrasive conduit seal member. In a microabrasion application, this makes it so that microabraded skin particles are collected downstream of the abrasive member and from all locations surrounding the abrasive member. In other applications (but also in microdermabrasion), such an arrangement assists in the ability to move the device in any direction over the skin. The symmetric nature of the configuration avoids such need as experienced with other implements that have a certain directionality requirement (i.e., they must "point" in their direction of travel). In a microdermabrasion application, the inventive device configuration provides for applying not only any abrasive compounds as may be desired directly and immediately at the spot of abrasion, but also (or alternatively) other solutions or compounds offering various benefits.

These and other objects, advantages, and features of the invention will become apparent to those persons skilled in the art upon reading the details of aspects of the invention as more fully described below.

BRIEF DESCRIPTION OF THE DRAWINGS

A more complete understanding of the devices, system, and methods according to the present invention may be obtained by referring to the following detailed description together with the accompanying drawings briefly described hereinafter. Comparable elements in the figures share the same or similar numbering.

FIG. 8A provides views of a panel of sealing and tissue abutment members.

FIG. 8B shows readable media which provides instructions for using the panel of sealing and tissue abutment members.

DETAILED DESCRIPTION OF THE INVENTION

Figure 1A:
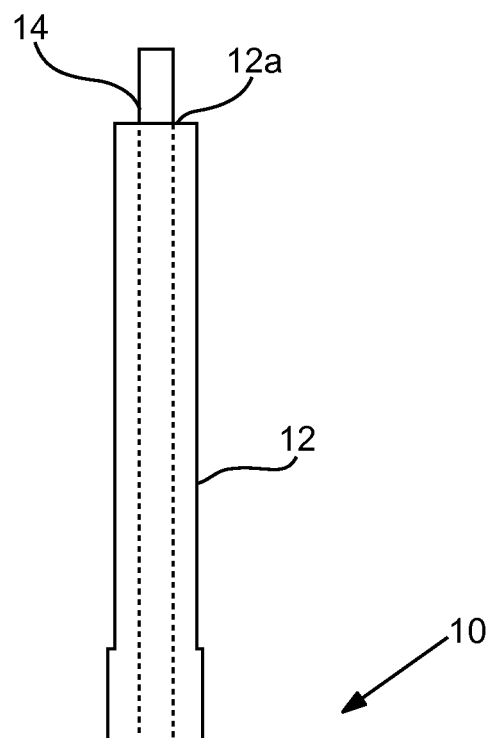
FIG. 1A is a partially exploded view of a microabrasion or skin treatment device according to the present invention.

Before the present device, system and methods are described, it is to be understood that this invention is not limited to particular structures described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise below, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods or materials, or combination, in connection with which the publications are cited.

It must be noted that as used herein and in the appended claims, the singular forms "a," "and," and "the" include plural referents unless the context clearly dictates otherwise. Thus, for example, reference to "a vacuum tube" includes a plurality of such vacuum tubes and reference to "the vacuum tube" includes reference to one or more vacuum tubes, to include a plurality of tubes interconnected in series, and equivalents thereof known to those skilled in the art, and so forth. More particularly, it is also understood that if an element is described as being connected to a vacuum source, that this description also includes the element being connected to an intermediate element, such as a tube or a filter, which is in turn connected to the vacuum source.

The publications discussed herein are provided solely for their disclosure prior to the filing date of the present application. Nothing in this application is to be construed as an admission that the present invention is not entitled to antedate such publication by virtue of prior invention. Further, the dates of publication provided may be different from the actual publication dates which may need to be independently confirmed.

The present invention provides the ability to perform microdermabrasion with or without flowing abrasive particles to be applied to the skin, with the ability to pretreat or condition the skin prior to microabrading it. The present invention further provides more efficient and complete removal of microabraded particles with the enveloping arrangement of the vacuum and, optionally, fluid flow that surrounds an abrasive member provided. Furthermore, the invention provides for application of therapeutic formula, in aid of microabrasion or for its own purpose.

The term "tube," "tubular," or "conduit" refers to a structure having a hollow, bore or through passage, or other passageway, substantially aligned along a longitudinal axis of the structure and which may have various cross sections. Thus, these terms refer not only to a common tube having a circular cross section with a central opening, but also to other structures including those having square, elliptical, or nongeometric and even irregular cross sections, which include such a passageway.

The term "tip" refers to the end of a structure or assembly. As used herein, the applicator tip is that component, whether integral or attachably fixed to the device, which is the endmost extremity of the device and is used in contacting the skin.

A "vacuum line" as used herein is a tubular structure that interconnects other components of the system so as to form a vacuum pathway therebetween.

Figure 1B:
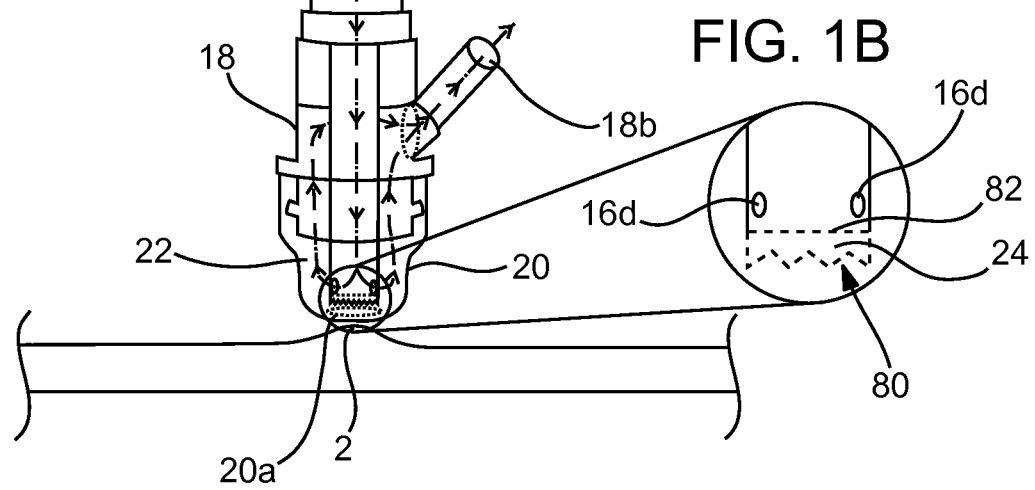
FIG. 1B is a detail of a portion of the device in FIG. 1A.
Figure 2:
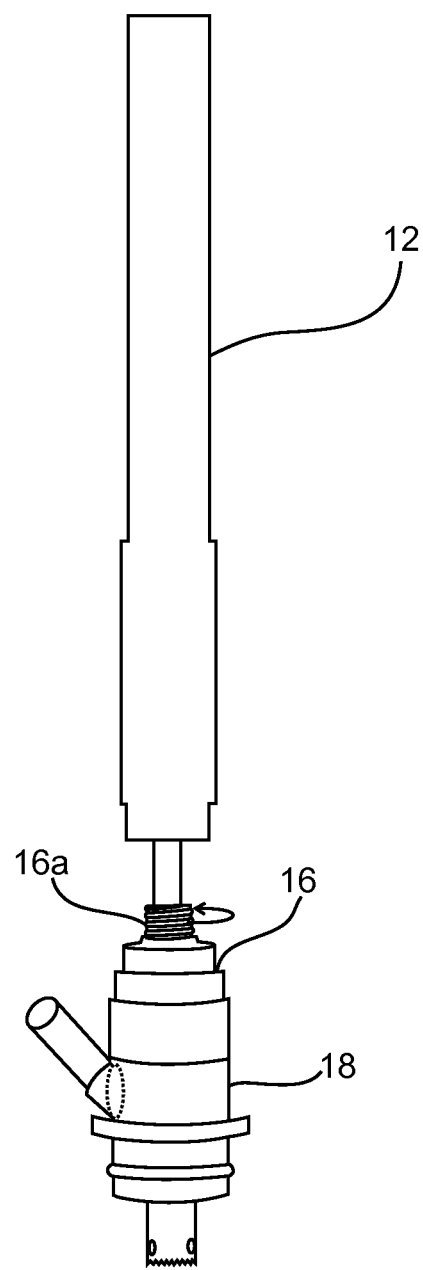
FIG. 2 is a partially exploded view of a microabrasion device with a tip of the device removed.

FIG. 1A shows a partially exploded view of a microabrasion or skin treatment device 10 according to the present invention. A portion of the same is detailed in FIG. 1B. Device 10 is designed to be handheld by a user for its application to the skin of a patient in the performance of microdermabrasion or other vacuum therapy applications. As such, it may be designed with an elongated handle 12 to facilitate grasping by a user. One of ordinary skill in the art will appreciate that many different shapes and materials may be employed for the handle 12 and the present invention is not to be limited to an elongated, substantially cylindrical handle 12 as shown. In the example of FIG. 1, handle 12 is made of plastic, such as nylon or other plastic having sufficient toughness and mechanical strength, but may also be made of metal, such as stainless steel, for example, or ceramics or composites. Handle 12 is annular or tubular, providing a passageway 12a through which tube 14 is extended.

Figure 3:
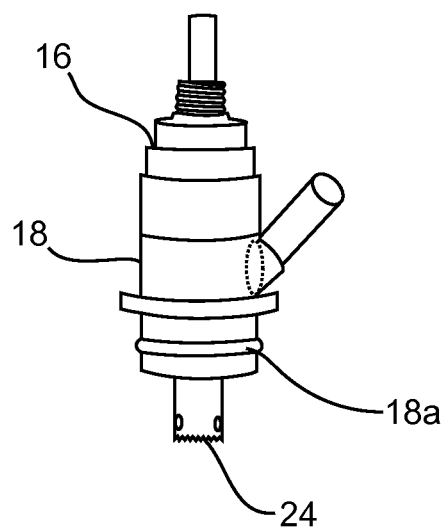
FIG. 3 is a view of an assembly including a vacuum head base and cannula with abrasive member according to the present invention.
Figure 5:
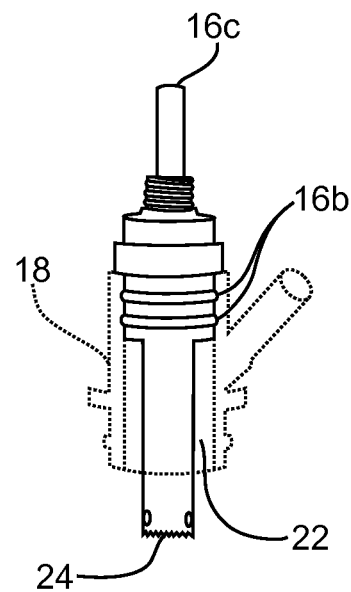
FIG. 5 is a view of a cannula with abrasive member according to the present invention.

Tube 14 is adapted to be connected at its proximal end 14a (the end extending away from handle 12) to a fluid reservoir 70 (described below in reference to FIGS. 6 and 8A) which is in turn, open to atmosphere. Tube 14 is flexible and may be made of PVC or other compatible plastic, for example. Similarly, all other vacuum lines described herein are flexible to afford maneuverability to device 10 and may be made of PVC or other compatible plastic. Alternatively, the proximal end of tube 14 can be left open to atmosphere or connected to a flow control valve or filter, or both, with or without connection to fluid reservoir 70. The distal end 14b of tube 14 is connected to cannula 16. Cannula 16 is adapted to be fixed to handle 12 and may be machined from metal such as surgical stainless steel or may be machined or molded of plastic or cast or molded from ceramic. Cannula 16 runs through the center of the handpiece Vacuum head base 18 is fitted over functional block 16, as shown in FIG. 3, for example, to form a pressure tight seal therewith. Vacuum head base 18 may be machined from machined from metal such as surgical stainless steel or may be machined or molded of plastic or casted or molded from ceramic. Vacuum head base 18 may be frictionally fit over functional block 16 with a seal being effectuated by positioning of one or more O-rings 16b (see FIG. 5) or other sealing members between functional block 16 and vacuum head base 18.

Figure 4:
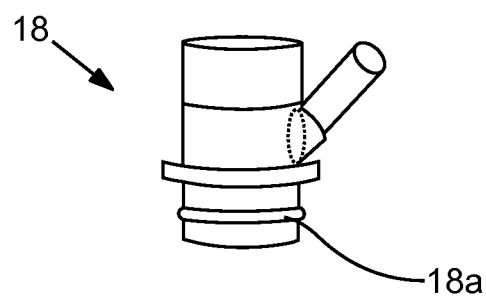
FIG. 4 is a view of a vacuum head base according to the present invention.

A treatment tip 20 is fitted over the end of vacuum head base 18, and, likewise may be friction fit or provided with threads or other attachment means, or any combination of these, to provide a pressure tight fit between the components. The tip is smooth surfaced and adapted to glide over the skin surface for application of lotions or vitamins, or both, or other fluids thereto during processing. The tip may be made of plastic such as nylon or glass, such as pyrex, for example and is preferably, although not necessarily transparent or translucent. A transparent tip allows better visualization by the operator during processing. One or more O-rings 18a (see FIG. 4) or other sealing members may be provided between vacuum head base 18 and tip 20 to facilitate the pressure tight seal. Alternatively, tip 20 may be integrally machined or molded with vacuum head base 18. Tip 20 includes an opening 20a which targets an area of skin to be contacted (e.g., to be microabraded) when tip 20 is applied to the skin. Although shown with a single large opening 20a, it is conceivable that tip 20 could be provided with more than one opening to perform a similar function as described below, in which case, multiple skin-opposing surfaces may be provided.

Functional block 16 is a tubular structure that is configured to mate with vacuum head base 18. Vacuum head base 18 is also a tubular structure which has a significantly larger inside diameter than the outside diameter of the distal portion of functional block 16, so as to form an annulus 22 therebetween. Tip 20 extends the annular space 22, as shown in FIG. 1. A passageway 16c runs the full length of functional block 16 and forms a continuation of the flow path defined by tube 14 when tube 14 is connected to the proximal end of functional block 16. A tip member 24 (e.g., abrasive members 24A, 24B, or 24C or nonabrasive member 24D of FIG. 8A) is formed at the distal end of functional block 16 thereby closing off the passageway 16c at the distal end of functional block 16. The abrasive member 24A, 24B, or 24C is formed by fusing abrasive particles to the end of the functional block 16, or could alternatively be made as an abrasive disk and fitted within an open end of the functional block to seal the end or mounted to a closed end of a functional block 16. Other removable and or replaceable configurations are possible as well.

The invention may also employ a nonabrasive member 24D that creates a seal due to the vacuum created from vacuum head 18. Such an alternative end configuration is best indicated in FIG. 1B by way of a hashed line tip 80 where abrasive material would otherwise be set. Like the abrasive end feature of device 10, a less abrasive sealing portion 24C or nonabrasive sealing portion 24D may be provided as a removable or replaceable member or segment. This potential is illustrated by virtue of dashed line 82 indicating a possible separation line between the main body of block 16 and sealing portion 24 (FIG. 1).

Although the abrasive or nonabrasive sealing member shown is substantially planar, it may alternatively be rounded, flared, concave, convex, or elongated, for example. For an abrasive tip, the abrasive particles are generally of a size ranging from about 50 to 300 grit, typically about 100 to 120 grit and are typically carborundum (aluminum oxide) or sodium bicarbonate, or the like. The coarser particles (at the lower ends of the grit ranges) may be provided for use in initial treatments, while finer particles (at the higher ends of the grit ranges) may be employed for subsequent treatments. Alternatively, the abrasive member may be formed by knurling, machining, laser treatment, or otherwise mechanically or chemically treating a closed end of the functional block or cannula end as discussed below.

As shown in FIG. 8A, in some instances it may be desired to provide a kit or panel 90 of abrasive and nonabrasive sealing members 24A, 24B, 24C, and 24D that vary from most abrasive to smooth or substantially smooth (or nonabrasive) that are fitted at the end of functional block 16. These may be intended for sterilization and repeated use or as disposables. Threadings 92 may be utilized to attach any of the sealing members 24A-24D to the device. The length "L" of such members may vary, as may other dimensions. However, the length will generally be coordinated with that of the member to which it is attached in order that the surface (abrasive or nonabrasive) will form a limiting surface for tissue drawn into tip opening 20a. Such contact is obviously necessary to enable dermal abrasion. It is also useful in the context of vacuum massage application in order to avoid drawing tissue too far into opening 20a such that it is bruised or otherwise damaged.

As shown in FIG. 8B, instructions as to treatment regimen or procedures in connection with the inventive hardware may be provided on any readable medium 100, including paper stock or a computer readable medium, or combination of these. Both the panel and instructions may be provided in packaged combination alone or with such other hardware as shown in the figures to provide a kit. Alternatively, the endpiece kit 90 may be provided separately though they are shown associated in FIGS. 8A and 8B.

One or more openings 16d are provided through the wall of the distal tubular structure of functional block 16 to establish one or more flow pathways between passageway 16c and annulus 22. Tip 20 extends beyond the extremity of functional block 16 such that member 24 is positioned internally of the assembled device 10, and surrounded by annulus 22.

An opening or port 18b is provided in vacuum head base 18 for connection of a vacuum source, for example, by connecting the vacuum port 18b to the vacuum source via a vacuum line. When vacuum is applied through opening 18b an opening 20a is sealed off, for example by placing it up against skin tissue, a closed loop vacuum flow path is established between the vacuum source and connecting line, vacuum opening 18b, annulus 22, opening or openings 16d, passageway 16c and tube 14. This flow path is shown in FIG. 1.

Figure 7A:
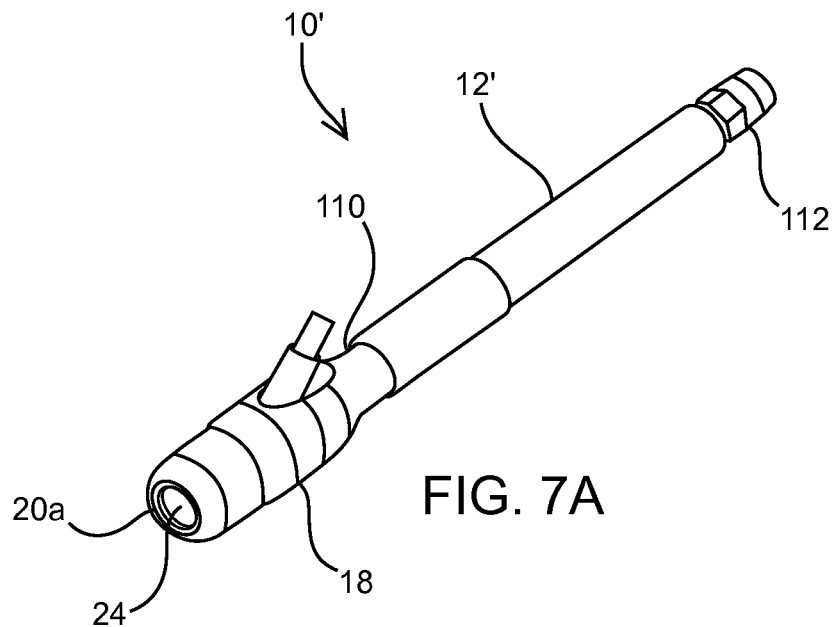
FIGS. 7A-7C show views of an alternate microabrasion or skin treatment device according to the present invention.
Figure 7B:
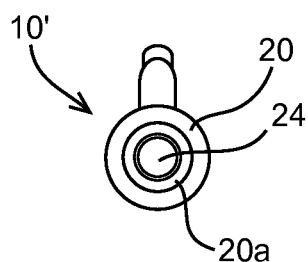
Figure 7C:
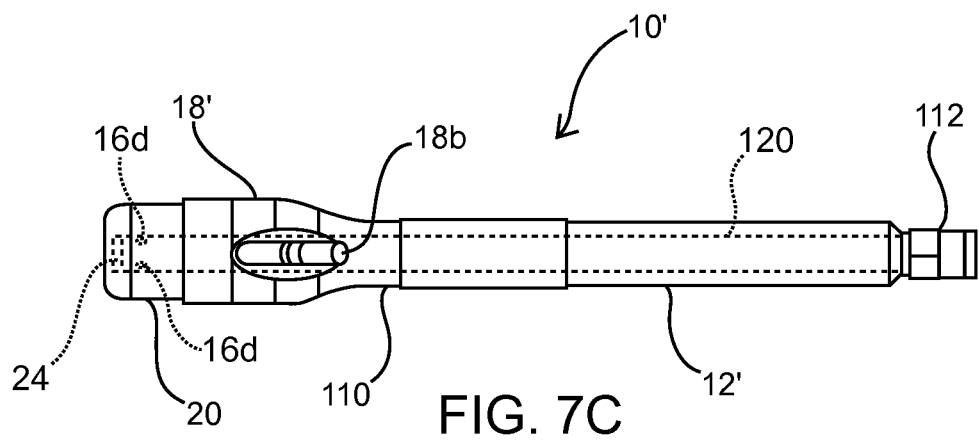

FIGS. 7A-7C show an alternative construction of the microdermabrasion device. Whereas the previous device 10 utilized a separate handle 12 and vacuum head base 18, these elements are integrated in device 10' in element 110. Still further, in the variation of the wand shown in FIGS. 7A-7C (especially as illustrated in FIG. 7C by virtue of the use of hidden line) a separate functional block 16 and line 14 within the handle may be abandoned in favor of a single tube or cannula 120. This member—closely fit within the integrated handle section 12' but leaving space within the integrated vacuum base region 18'—preferably comprises stainless steel and includes threaded end sections to receive a threaded end fitting 112 and threadings 92 of a member 24 that acts as a stop. Naturally, other materials and constructional options such as press-fitting, bonding, welding, and so forth may be employed as to these referenced elements. However, the connector is preferably a quick connect/disconnect fitting as shown enabling simple separation, sterilization, or swap-out, or combination of these. Of course, other variations in the microdermabrasion device or wand configuration are possible as well.

Figure 6:
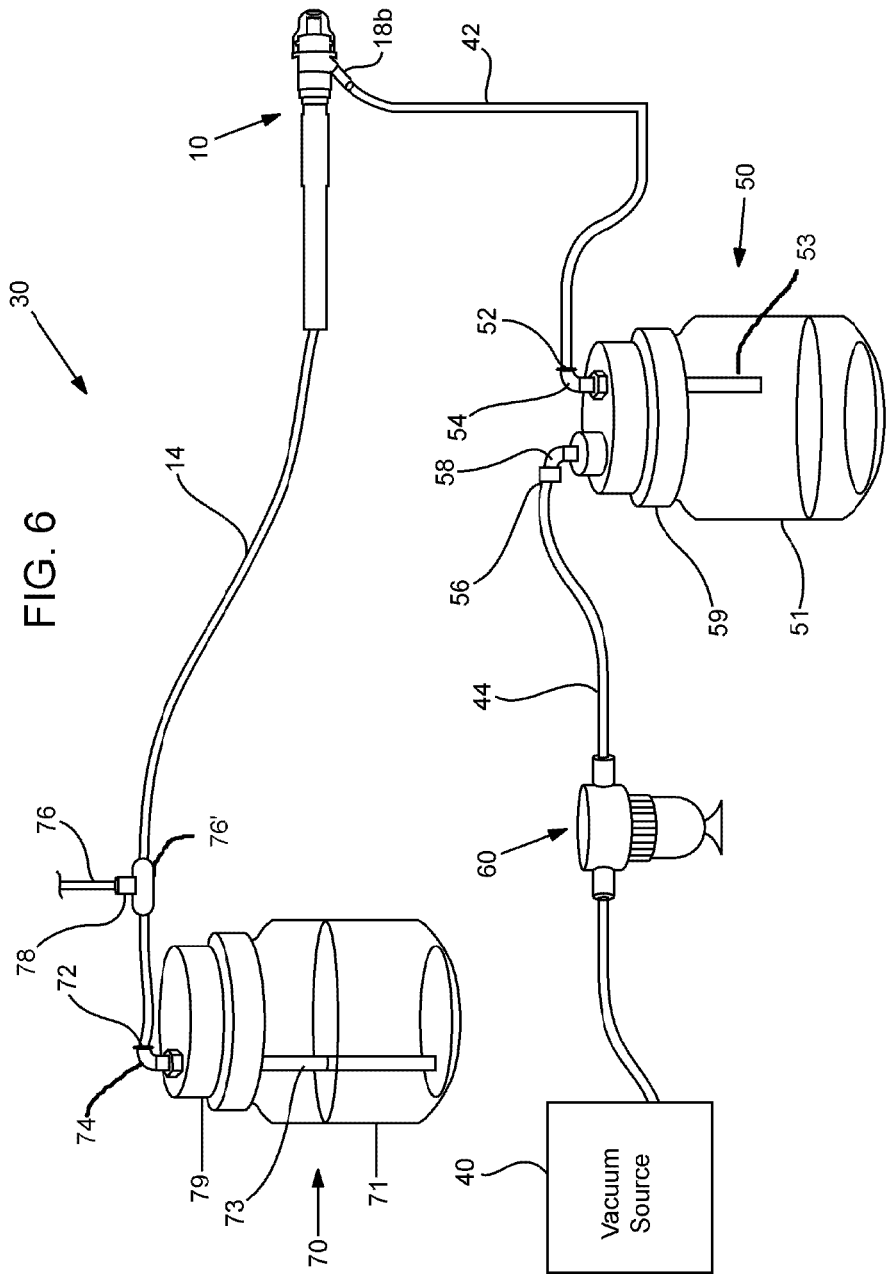
FIG. 6 is a schematic of a microdermabrasion system according to the present invention.

FIG. 6 shows an example of a microdermabrasion system 30 according to the present invention, which incorporates device 10 or 10' (though only device 10 is shown). Vacuum opening 18b is connected with a vacuum source 40 as described above, by vacuum line 42. A collection reservoir 50 and, optionally, an inline filter 60 are connected in the vacuum line between device 10 and vacuum source 40. Vacuum line 42 connects to an input 52 to collection reservoir 50 via elbow 54, for example, and output 56 connects with a second vacuum line 44 via elbow 58, for example. A manifold cover 59 sealably interfaces the input (52, 54) and output (56, 58) connections with a reservoir 51 which is typically a jar made of glass or plastic for example. An extension tube 53 connects with input 52, 54 and extends into the reservoir 51 to ensure effective delivery of waste materials (abraded skin particles and, optionally, fluids) to reservoir 51.

Optionally, a back-up filter 60 may be provided inline between vacuum lines 44 and 46 as added insurance that no or substantially no fluid, skin particles, abrasive particle or other materials being collected by collection reservoir 50 can be transported to vacuum source 40. Filter 60 may be an in-line condensation filter, such as water condenser produced by Wilkerson Labs and available as part number F0001-000 from Nor-Cal Controls, Inc. of Santa Clara, Calif.

The vacuum source may be the same as that provided for currently existing microdermabrasion devices, such as the ProPeel, MDPeel, or iPeel, for example, each available from emed, Inc., Westlake Village, Calif. A power switch is used to activate the vacuum source and a vacuum in the range of about 2 to 14 pound per square inch (psi) is generally used during a procedure, depending upon the skin condition of the person being treated.

Tube 14 extends from the proximal end of the microdermabrasion device 10, and connects with output 72 of fluid reservoir 70 via elbow 74, for example. A breather line 76 may be connected inline via T-joint 76', for example, or other interconnection, and includes an adjustable valve 78 or other means for varying an amount of air that is allowed into the tube 14. This feature not only allows the amount of vacuum to be adjusted for a given fluid, but allows fluids having different viscosities to be applied at the same vacuum level, since different viscosities will require varying amounts of air to be inletted through the breather line, to give a constant vacuum level. Alternatively, a breather line or input with adjustment valve may be located on elbow 74 or directly on manifold cover 79. Still further, a valve or other flow control mechanism may be provided in the fluid delivery line 14 to control the amount of liquid passing through the line. This feature can be provided alternatively, or in addition to the breather line discussed above. An input is provided in manifold which is open to atmosphere to prevent vacuum buildup in reservoir 70. A manifold cover 79 sealably interfaces the input output (72, 74) connections with a reservoir 71 which is typically a jar made of glass or plastic, for example, and contains lotions, vitamins or other skin treatment fluids, or combination of these, to be applied to the skin through tip opening 20a. An extension tube 73 connects with output 72, 74 and extends into the reservoir 71 to near the bottom of the reservoir to ensure that most all of the contents of reservoir 71 are capable of being delivered through the system.

Abrasive particles, such as corundum crystals, sodium bicarbonate particles or other abrasive particles, including those disclosed in U.S. Pat. No. 5,971,999 (which is hereby incorporated in its entirety by reference thereto), for example may be included in reservoir 71 for delivery through the system to perform a microabrading function, although this is not the preferred configuration of the present invention, as sufficient microabrasion may be accomplished via abrasive member 24. If used, the abrasive particles may be used together with any of the fluids mentioned above or with some other fluid carrier medium, such as those described in U.S. Pat. No. 5,971,999, for example.

Reservoir 70 may contain solution or a suspension for purposes other than abrasion or pure abrasiveness. General examples, types or categories of compounds, or combination, that may be employed include: beaching formulations (e.g., 2-4 percent hydroquinone, 2 percent Kojic acid, 1 percent vitamin K, and 1 percent hydrocortisone in a aqueous base); acne treatment formulations (e.g., salyicilic acid, alcohol base buffered by witch hazel, etc.); fine lines/wrinkle treatment formulations (e.g., hyaluronic acid is an aqueous base); hydrating formulations (e.g., calendula, vitamins A, D, or E, or any combination, in a mineral oil base); antioxidant formulations/free radical; scavengers (e.g., vitamins A, E, and K in a mineral oil base). Other examples of product categories that may be employed alone or in combination with other compounds include, antiseptics, astringents, cleansers, pore decongestants, balms, botanicals, collagen stimulators, herbs, microemulsifiers, oxygen delivery vehicles, proteins, serums, skin firming agents, toners, topical anesthetics, and tyrosinase inhibitors. Individually named products as may be used (with associated benefit indicated parenthetically) include: aloe vera (calming); alpha hydroxy acids (peel); alphalipoic acid (antioxidant); benzoil and other peroxides (acne); ceramide (hydrator); copper (toning); copper peptide (toning); CoQ-10 (coenzyme Q-10) and other enzymes (toning); cortisone (calming); glycolic acids (peel); hyaluronic acid (collagen stimulation); hydrolipids (hydrator); hydroquinones (bleaching); lactic acids (peel); magnesium ascorbic phosphate (free radical scavenger, collagen stimulator, bleaching); niacin (vascular dilation); phospholipids (moisturization); potassium (toning, psoriasis), and salyicilic acids (acne). Of course, any combination of such elements may be provided—even in connection with abrasive particles.

Note, however, the present system may be used by eliminating the fluid reservoir 70 altogether, where microdermabrasion is performed in a "dry state" and tube 14 is simply left open to atmosphere, with or without a filter or valve, or combination, for adjusting the amount or flow rate of air that is allowed into tube 14. Similarly, dry or externally lubricated vacuum massage of tissue may be accomplished in instances where a nonabrasive sealing member 24D is employed.

For use in microdermabrasion, device 10 is positioned so as to place tip 20 in contact with the skin surface to be microabraded and the vacuum source is turned on to establish a vacuum within the system 30. It should be noted here that the order of positioning and turning on the vacuum is not critical as the vacuum can be turned on prior to contacting the tip 20 with skin, since the vacuum loop will not be closed until such time that opening 20a is sealed by the skin.

Upon forming the vacuum loop as described above, the fluid contents in fluid reservoir 70 are drawn through tube 14 and into device 10 where they flow out of the cannula 16 through openings 16d and are applied to the skin. A targeted area of the skin (which is defined by the perimeter of the opening 20a is drawn up into the tip 20 and a central portion of the targeted area of skin is drawn into contact with abrasive member 24, while portions of the targeted area surrounding the central portion are treated with the fluid contents. As the user or operator of the device 10 glides the tip 20 over the surface of the skin, the targeted area in contact with the abrasive surface 24 is scraped over the abrasive surface where microdermabrasion of that portion of the skin is performed. Continued movement of the tip over the skin likewise continues the microdermabrasion of the targeted area, which changes along with the movement of the tip.

Advantageously, since the flow of fluids surrounds the area of skin being microabraded, the skin is both pretreated and posttreated with the vitamins, lotions, etc. contained in the reservoir 70. Pretreatment can soften the area of skin treatment to be microabraded, thereby rendering exfoliation more complete and easier to accomplish with less trauma to the skin tissues left behind, while posttreatment helps to reduce streaking and redness of the skin tissues left behind.

As the flow of the fluids continues out of the vacuum head base and into vacuum line 42, it carries with it the exfoliated skin particles and any other waste that is removed through the microdermabrasion process. Since the fluids surround the abrasive member 24, they are very effective in taking up substantially all of the particles that are loosened during the microdermabrasion process, in contrast with prior art mechanisms having a abrasive tip that can only vacuum up particles from the leading portion of the tip (through a central opening through the abrasive tip), while all of the particles that are loosened or freed up by the trailing side of such a tip (i.e., that portion of the abrasive tip that is behind the central opening with respect to the direction of movement over the skin) are left behind.

When the invention is to be employed for vacuum massage and treatment with a nonabrasive tissue-opposing surface, the procedure is substantially the same. However, the motion employed in use may differ, as may the areas of coverage. Particularly, more sensitive areas such as the lips may be more appropriately targeted than would otherwise be the case.

Although the abrasive or nonabrasive member 24 and cannula 16 described herein are example of constructing the device according to the present invention, it is noted that they need not be constructed in this exact manner, as other configurations could be assembled to carry out the invention as described. For example, an abrasive or nonabrasive member similar to that described, could be mounted to the inner walls of a vacuum head base with several spokes, while still maintaining an annulus substantially around the perimeter of the abrasive member, with the remainder of the cannula then simply being replaced by an extension of tube 14.

Also, the abrasive or nonabrasive member could be formed in different shapes such as square or any other shape that substantially maintains an annulus or other flow paths that would substantially surround the abrasive member with fluid flow as described. Still further, the abrasive or nonabrasive member could be mounted in the vacuum head base so as to allow flow channels only over upstream and downstream perimeters of the same, while leaving no openings along the side perimeters of the abrasive or nonabrasive member which could be welded or otherwise sealed against the inner walls of the vacuum head base. Such a configuration would still allow leading edge and trailing edge uptake of microabraded skin particles and/or liquid that is delivered within annular space 22. However, an annulus or other flow configuration which flows over substantially the entire perimeter of the abrasive member is preferred. Such a configuration is particularly more effective when circular movements of the tip 20 over the skin are applied. Indeed, it is efficacious in situations where movement in changing directions is desired since the instrument is not "pointing" in any particular direction as may be the case with other devices.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

The invention claimed is:

1. A method comprising:
applying a treatment tip to a skin surface, wherein the treatment tip is removably coupled to a distal end of a handle;
providing a suction through at least one opening of the treatment tip to establish an annular region of the suction, wherein the annular region at least partially surrounds a smooth surface, wherein the smooth surface is substantially planar and is coupled to the distal end;
drawing a portion of the skin surface into contact with the smooth surface using the suction;
providing a fluid to the skin surface to an area inside a periphery of the smooth surface, wherein the fluid passes from a proximal end of the handle to the distal end; and
moving the treatment tip over the skin surface.

2. The method of claim 1 further comprising removing and replacing the treatment tip with another treatment tip comprising an abrading surface.

3. The method of claim 1 wherein the fluid comprises a hydroquinone.

4. The method of claim 1 wherein the fluid comprises 2-hydroxymethyl-5-hydroxy-γ-pyrone.

5. The method of claim 1 wherein the fluid comprises vitamin K.

6. The method of claim 1 wherein the fluid comprises a 2-methyl-1,4-naphthoquinone derivative.

7. The method of claim 1 wherein the fluid comprises magnesium ascorbyl phosphate.

8. The method of claim 1 wherein the fluid comprises hydrocortisone in an aqueous base.

9. The method of claim 1 wherein the fluid comprises tyrosinase inhibitors.

10. The method of claim 1 wherein the fluid comprises a bleaching formulation.

11. The method of claim 1 wherein the treatment tip comprises a first length L1 and the method further comprises:
replacing the treatment tip of length L1 with another treatment tip comprising a second length L2, wherein L2 is a different length than L1, and a length of the treatment tip limits an amount of the skin surface that is drawn toward the at least one opening of the treatment tip.

12. The method of claim 1 wherein the treatment tip comprises a first length L1 and the method further comprises:
replacing the treatment tip of length L1 with another treatment tip comprising an abrasive surface and a second length L2, wherein L2 is a different length than L1, and a length of the treatment tip limits an amount of the skin surface that is drawn toward the at least one opening of the treatment tip.

13. The method of claim 1 wherein the drawing a portion of the skin surface into contact with the smooth surface using the suction comprises:
causing the skin surface to elevate with respect to surrounding skin.

14. A method comprising:
applying a treatment tip to a skin surface, wherein the treatment tip is removably coupled to a distal end of a handle;
providing a suction through at least one opening of the treatment tip to establish an annular region of the suction, wherein the annular region at least partially surrounds a smooth surface, wherein the smooth surface is substantially planar and is coupled to the distal end;
drawing a portion of the skin surface into contact with the smooth surface using the suction, wherein the portion of the skin surface drawn into contact with the smooth surface becomes elevated with respect to surrounding skin;
providing a fluid to the skin surface to an area inside a periphery of the smooth surface, wherein the fluid passes from a proximal end of the handle to the distal end; and
moving the treatment tip over the skin surface.

15. The method of claim 14 wherein the treatment tip comprises a first length L1 and the method further comprises:
replacing the treatment tip of length L1 with another treatment tip comprising a second length L2, wherein L2 is a different length than L1, and a length of the treatment tip limits an amount of the skin surface that is drawn toward the at least one opening of the treatment tip.

16. The method of claim 14 further comprising removing and replacing the treatment tip with another treatment tip comprising an abrading surface.

17. The method of claim 14 wherein the fluid comprises a hydroquinone.

18. The method of claim 14 wherein the fluid comprises 2-hydroxymethyl-5-hydroxy-γ-pyrone.

19. The method of claim 14 wherein the fluid comprises a 2-methyl-1,4-naphthoquinone derivative.

20. The method of claim 14 wherein the fluid comprises hydrocortisone in an aqueous base.

* * * * *